(12) United States Patent
Lu (10) Patent No.: US 9,925,179 B2
(45) Date of Patent: Mar. 27, 2018

(54) COMBINATION THERAPY FOR MENTAL DISORDERS

(71) Applicant: Ru-Band Lu, Tainan (TW)

(72) Inventor: Ru-Band Lu, Tainan (TW)

( * ) Notice: Subject to any disclaimer, the term of this patent is extended or adjusted under 35 U.S.C. 154(b) by 0 days.

(21) Appl. No.: 15/589,276

(22) Filed: May 8, 2017

(65) Prior Publication Data
US 2017/0258779 A1 Sep. 14, 2017

Related U.S. Application Data

(63) Continuation-in-part of application No. 14/807,927, filed on Jul. 24, 2015, now abandoned.

(60) Provisional application No. 62/031,825, filed on Jul. 31, 2014.

(51) Int. Cl.
*A61K 31/473* (2006.01)
*A61K 31/13* (2006.01)

(52) U.S. Cl.
CPC ............ *A61K 31/473* (2013.01); *A61K 31/13* (2013.01)

(58) Field of Classification Search
None
See application file for complete search history.

(56) References Cited

U.S. PATENT DOCUMENTS

2010/0297181 A1* 11/2010 Hanada .............. A61K 31/4412
424/239.1

OTHER PUBLICATIONS

Lee et al., The DRD2/ANKK1 gene is associated with response to add-on dextromethorphan treatment in bipolar disorder, Journal of Affective Disorders 138 (2012) 295-300.*
Koukoloupos et al., The sustained mood-stabilizing effect of memantine in the management of treatment resistant bipolar disorders: Findings from a 12-month naturalistic trial, Journal of Affective Disorders 136 (2012) 163-166.*

* cited by examiner

*Primary Examiner* — Svetlana M Ivanova
(74) *Attorney, Agent, or Firm* — Hannah M. Tien (57) ABSTRACT

The present invention relates to a method of decreasing cholesterol or low density lipid protein in a subject in need thereof comprising: administering to said subject a pharmaceutically effective amount of a composition comprising dextromethorphan.

The present invention also relates to a method of treating a subject suffered from bipolar II disorder, comprising administering to said subject a therapeutically effective amount of valproic acid and a combination of dextromethorphan and memantine, wherein the dose of dextromethorphan or memantine is a low dose not sufficient to work as a N-methyl-D-aspartate (NMDA) receptor antagonist.

The present invention further relates to a composition for treating bipolar II disorder, which comprises valproic acid and a combination of dextromethorphan and memantine, wherein the dose of dextromethorphan or memantine is a low dose not sufficient to work as a N-methyl-D-aspartate (NMDA) receptor antagonist.

3 Claims, 5 Drawing Sheets

COMBINATION THERAPY FOR MENTAL DISORDERS

CROSS-REFERENCES TO RELATED APPLICATIONS

The present application claims priority to U.S. Provisional Application No. 62/031,825 filed on Jul. 31, 2014, and U.S. Non-provisional application Ser. No. 14/807,927 filed on Jul. 24, 2015, which are incorporated herein by reference in their entireties.

FIELD OF THE INVENTION

The present invention relates to novel uses of dextromethorphan and memantine.

BACKGROUND OF THE INVENTION

Bipolar disorder (BP) characterized by a dysregulation of mood, impulsivity, risky behavior, and interpersonal problems, is a recurrent and often chronic psychiatric illness. According to the World Health Organization (WHO), BP is the sixth leading cause of disability-adjusted life years worldwide among persons aged 15 to 44 years. It is associated with functional impairment, elevated suicide rates, and utilization of mental health systems.

BP is known for recurrent depressive, manic, and mixed episodes, and BP is divided into several categories. However, BP is commonly under-recognized, even in psychiatric settings. Increasing evidences suggest that neuronal degeneration may relate to the etiology and progression of bipolar disorder. Imaging studies suggest that ongoing neuronal atrophy accompanies the disorder. For instance, PET images of the cerebral blood flow and the rate of glucose metabolism, both indicative of brain activity, detect a reduced activity in the subgenual prefrontal cortex during the bipolar depression. This decrement in activity in part corresponds to a reduction of cortical volume, similar in a manner to that seen in magnetic resonance imaging demonstrating the reduced mean volume on grey matters. In BP, abnormalities of the third ventricle, frontal lobe, cerebellum, and possibly the temporal lobe are also noted. These observations suggest a neuronal dysfunction and possibly neuronal loss may be involved in the pathogenesis of BP. Therefore, BP may represent a neuro-degeneration disease.

In addition, BP may be associated with induction of a lot of endotoxins and exotoxins which may increase neurotoxins as well as decrease of neurotrophic factors duo to overactivate microglial cell and inhibit astroglia cell. Those effects may induce pre-inflammatory factors such as TNF-α, C-reactive protein, interleukins, etc. and decrease BDNF etc. which will cause neuron damage or necrosis. The vicious cycle will lead to progressive worsening of the disease.

While the pharmacological guidelines for treatment are well established, treatment for BP remains less than ideal. Most individuals still have breakthrough episodes or significant residual symptoms while on medication. In addition, functional deficits often remain even when patients are in remission. Moreover, most BP patients are newly diagnosed who have not taken any mood stabilizer or antipsychotics in the past. Because many patients with BP remain symptomatic even when fully adherent to their medication regimens, greater understanding of the pathogenesis of this illness and novel treatment modality other than current regimen of mood stabilizers and antipsychotics is needed.

Cholesterol is an organic molecule. It is a lipid molecule and is biosynthesized by all animal cells because it is an essential structural component of all animal (not plant or bacterial) cell membranes that is required to maintain both membrane structural integrity and fluidity. Cholesterol travels through bloodstream in small packages called lipoproteins. These packages are made of fat (lipid) on the inside and proteins on the outside. Two kinds of lipoproteins carry cholesterol throughout body: low-density lipoproteins (LDL) and high-density lipoproteins (HDL). Having healthy levels of both types of lipoproteins is important. LDL cholesterol sometimes is called "bad" cholesterol. A high LDL level leads to a buildup of cholesterol in arteries. HDL cholesterol sometimes is called "good" cholesterol. This is because it carries cholesterol from other parts of body back to liver, so that liver can remove the cholesterol from body. High cholesterol level increases the risk of some conditions, such as coronary heart disease, stroke, peripheral vascular disease, type 2 diabetes, and high blood pressure. Therefore, a method for decreasing cholesterol or LDL level in body is needed.

Dextromethorphan (DM) has been used as an antitussive drug with little side effect for more than 50 years in clinics. It is known to have a wide margin of safety. DM has been shown to be neuroprotective in rodents and protects the 1-methyl-4-phenyl-1,2,3,6-tetrahydropyridine (MPTP)- or lipopolysaccharide (LPS)-induced dopaminergic neuronal damage in vitro and in vivo. Furthermore, DM also protects against the ischemia-induced neuronal damage in rats and has been reported to have neuroprotective effect on monoamine neurons and to have protective effect against endotoxicity and extratoxicity. DM has neuronal protective effects in high dose and low dose. However, the high dosage of DM may cause side effects including body rash/itching, nausea, vomiting, drowsiness, dizziness, constipation, sedation, confusion, nervousness, and closed-eye hallucination. The high dosage of DM may not only increase side effect but also confuse the detailed mechanism of medication; the low dosage will demonstrate the specific effect of the DM in the decrease of cytokine including TNF-α and neuroprotective effect. The mechanism of the neuroprotective effects of low dose DM is associated with the inhibition of microglia activation but not with its N-methyl-D-aspartate (NMDA) receptor antagonist property. Moreover, a better correlation is found between the anti-inflammatory potency and the neuroprotection of low dose DM. These results suggest that the neuroprotection provided by low dose DM in the inflammation-related neurodegenerative models is not mediated through the NMDA receptor. U.S. Pat. No. 8,785,472 (Publication No. 2011/0281904 A1) suggests that DM is effective in the treatment of BP patients. In addition, low plasma levels of DM (5-100 ng/ml) found in these patients suggests that this beneficial effect of low dose DM is not mediated through the blockade of NMDA receptors. The clinical studies have indicated that patients taking 30-60 mg/70 kg of DM showed plasma DM concentrations of about 10-30 ng/ml (28-84 nM) which is not effect in NMDA receptor. The same low dose of DM causes a significant anti-inflammatory as well as a BDNF-increasing effect in bipolar disorder patients.

Memantine used to be recognized as a noncompetitive N-methyl-D-aspartate receptor antagonist. It was found to have neuroprotective effect in several neurodegenerative diseases in the past years. Memantine can inhibit brain inflammatory response through its action on neuroglial cells and provide neurotrophic effect. Mechanistic studies reveal that the high potency of small dosage of memantine is due to its dual actions: an anti-inflammatory effect by reducing the activity of microglia and an increase in the release of neurotrophic factors, such as BDNF, GDNF by astroglia (U.S. patent application Ser. No. 12/486,630 (Publication No. 2009/0253803 A1). It is also found that even ¹/₁₀₀ dosage of memantine (0.2 mg/kg) may be effective in opioid addictive behavior in rat by conditioned place preference.

SUMMARY OF THE INVENTION

The present invention relates to a method of decreasing cholesterol or low density lipid protein in a subject in need thereof comprising: administering to said subject a pharmaceutically effective amount of a composition comprising dextromethorphan.

The present invention also relates to a method of treating a subject suffered from bipolar II disorder, comprising administering to said subject a therapeutically effective amount of valproic acid and at least one agent selected from the group consisting of dextromethorphan and memantine. The present invention further relates to a method of treating a subject suffered from bipolar II disorder, comprising administering to said subject a therapeutically effect amount of valproic acid and a combination of dextromethorphan and memantine.

The present invention further relates to a composition for treating bipolar II disorder, which comprises valproic acid and at least one agent selected from the group of dextromethorphan and memantine. The present invention further relates to a composition for treating bipolar II disorder, which comprises valproic acid and a combination of dextromethorphan and memantine.

DETAILED DESCRIPTION OF THE INVENTION

The present invention is to investigate the efficacy of combination therapy of add-on low dose dextromethorphan (DM) and memantine, add-on DM, add-on memantine and placebo for bipolar II disorder (BP-II) treatment in a randomized, double-blind, placebo-controlled trial and will explore inflammatory and neurodegeneration to identify biological markers for predicting treatment response.

Also, the present invention is to investigate whether adding on dextromethorphan and memantine to valproate treatment has synergistic effect and show higher efficacy in improving symptomatology, anti-inflammatory factors, and plasma BDNF, cytokine levels and metabolic profiles in bipolar disorder or other major mental illnesses patients.

It is predicted that patients with altered expressions of inflammatory and neurodegeneration factors (e.g. BDNF, TNF-α, . . . ), lower plasma levels of BDNF, higher cytokine levels, and more severe baseline symptoms are more likely to benefit from such combination therapy.

The present invention also finds that dextromethorphan can decrease cholesterol or low density lipid protein in human.

Unless otherwise defined in the present context, the scientific and technical terms used in the present invention should possess meaning commonly known by any person with ordinary skill in the art. The meaning and scope of the terms should be clear; nevertheless, in any circumstance of discrepancy in the meaning, definition provided in the present context precedes those defined in any other dictionaries or external references.

The entire context of any references cited in the present context is incorporated into the present context as references.

Unless otherwise needed in the present context, singular terms should include plural forms and plural terms should include singular forms.

As used herein, the term "suppress", "decrease" or "reduce" or any variation of these terms when used in the claims and/or specification includes any measurable reduction or complete inhibition to achieve the desired result.

When the term "one" is used in conjunction with the term "comprising" in claims and/or specification, it means "one", but also equivalent to the meaning of "one or more", "at least one" and "one or more than one".

The term "or" used in the claims refers to "and/or" unless substitutes are mutually exclusive.

The term "about" in the full text of the present application refers to a value comprising inherent error differences derived from the methods or devices used for determining the value, or differences exist in the subjects.

As used in the specification and claims, the term "comprise" (and any form of comprise), "have" (and any form of have), "include" (and any form of include), or "contain" (and any form of contain) indicates inclusion rather than limitation. When a patent claim states that a particular product or method comprises certain elements, this means that other elements may also be present.

Therefore, the present invention provides a method for decreasing cholesterol or low density lipid protein in a subject in need thereof comprising: administering to said subject a pharmaceutically effective amount of a composition comprising dextromethorphan. This method can be used in treating diseases or conditions associated with high cholesterol, such as, for example, coronary heart disease, stroke, peripheral vascular disease, type 2 diabetes, high blood pressure, or hypercholesterolemia. In an embodiment, the dose of dextromethorphan is a low dose not sufficient to work as an N-methyl-D-aspartate (NMDA) receptor antagonist. For example, the dose of dextromethorphan may equal to or less than 60 mg/day. In an embodiment, the dose of dextromethorphan ranges from 10 mg/day to 60 mg/day. In an embodiment, the dose of dextromethorphan ranges from 30 mg/day to 60 mg/day.

The present invention also provides a method of treating a subject suffered from bipolar II disorder, comprising administering to said subject a therapeutically effective amount of valproic acid and at least one agent selected from the group consisting of dextromethorphan and memantine, wherein the dose of dextromethorphan or memantine is an ultra low dose not sufficient to work as an N-methyl-D-aspartate (NMDA) receptor antagonist. For example, the ultra low dose of memantine for human may range from about 1 mg/day to 10 mg/day, and the ultra low dose of dextromethorphan for human may range from about 10 mg/day to 60 mg/day. In an embodiment, the method administers to said subject a therapeutically effective amount of valproic acid and a combination of dextromethorphan and memantine. The combination of dextromethorphan and memantine produces a synergistic effect in treating bipolar II disorder. The ratio of dextromethorphan to memantine can be from 12:1 to 3:1. In an embodiment, the ratio of dextromethorphan to memantine is 6:1.

The present invention further provides a composition for treating bipolar II disorder, which comprises valproic acid and at least one agent selected from the group of dextromethorphan and memantine, wherein the dose of dextromethorphan or memantine is an ultra low dose not sufficient to work as an N-methyl-D-aspartate (NMDA) receptor antagonist. For example, the ultra low dose of memantine for human may range from about 1 mg/day to 10 mg/day, and the ultra low dose of dextromethorphan for human may range from about 10 mg/day to 60 mg/day. In an embodiment, the composition comprises valproic acid and a combination of dextromethorphan and memantine. The ratio of dextromethorphan to memantine in the composition can be from 12:1 to 3:1. In an embodiment, the ratio of dextromethorphan to memantine is 6:1.

The composition of the present invention further comprises a pharmaceutical carrier, buffer, diluent, or excipient. The suitable diluents are polar solvents, such as water, alcohol, ketones, esters and mixtures of the above solvents, preferably water, alcohol and water/alcohol mixture. For the preferable embodiment, the suitable solvents are water, normal saline, buffering aqueous solution and buffering saline etc. The excipients used with the composition of this invention can be in liquid, semi-liquid or solid form, such as lactose, dextrin, and starch and sodium stearate. Liquid excipients include water, soybean oil, wine and juices etc.

The composition of the present invention can be administered by oral or injection. The composition can be taken by oral in liquid, semi-liquid or solid form. The composition provided by injection is in liquid or semi-liquid form. The injection includes intravenous injection, the abdominal cavity and intramuscular injection.

EXAMPLES

The examples below are non-limiting and are merely representative of various aspects and features of the present invention.

Example 1

250~300 male and female BP-II patients (18~65 years old) were recruited, from the Department of Psychiatry at National Cheng Kung University Hospital and Tri-Service General Hospital into a 12-week treatment. The research protocol was examined for approval by the Institutional Review Board for the Protection of Human Subjects at National Cheng Kung University Hospital and Tri-Service General Hospital. All participants were given a complete description of the study and were asked to sign an informed consent before the study began. Patients who had major, mental illnesses other than BP-II and who had taken memantine or DM within 1 week before the first dose of the double-blind medication were excluded. The Chinese Version of Modified Schedule of Affective Disorder and Schizophrenia-Life Time (SADS-L) will be conducted for confirmation of the diagnosis. Although DSM-IV-TR (American Psychiatric Association, 2000) criteria require a minimum duration of 4 days of hypomania, current epidemiologic data suggest that a 2-day duration is more prevalent in community samples; therefore, the 2-day minimum for hypomania in the diagnosis of BP-II was used in this example. After each patient had been diagnosed based on DSM-IV criteria by a senior psychiatrist and confirmed by a clinical psychologist using a structured interview, SADS-L, the severity of each patient's clinical symptoms was assessed using the 17-item Hamilton Rating Scale for Depression (HRSD) and the Young Mania Rating Scale (YMRS). All the patients at Screen who score 18 on the HRSD or 14 on the YMRS were recruited. Eligible patients were randomly assigned into four treatment groups (n=40-45 for each group) in a double-blind manner and all groups matched in demographic characteristics, symptom severity, while they received open-label valproic acid (VPA) treatment (500 mg and 1000 mg daily [50-100 g/ml in plasma]): 1) DM (30 mg/day), 2) memantine (5 mg/day), 3) combination of DM and memantine (30 mg/day DM and 5 mg/day memantine), and 4) placebo respectively for 12 weeks. Patients were randomized into 4 groups through a computer-generated randomization table to receive placebo or any of active treatments in a 1:1:1:1 ratio. The patients with side-effect intolerance or clinical worsening were withdrawn earlier.

Patient Selection

Inclusion Criteria

1) Male or female patient aged ≥18 and ≤65 years.
2) Signed informed consent by patient or legal representative.
3) The Chinese version of the modified SADS-L, a semi-structured interview aimed at formulating the main bipolar II diagnoses based upon DSM-IV criteria with good inter-rater reliability. This modified version of SADS-L with its diagnoses was used as the gold standard.
4) A 2-day minimum for hypomania to diagnose BP-II.
5) A total of Hamilton Rating Scale for Depression (HDRS) scored at least 18 or Young Mania Rating Scale (YMRS) scored at least 14 at the screening stage.
6) Patient or a reliable caregiver was expected to ensure acceptable compliance and visit attendance for the duration of the study.

Exclusion Criteria

1) Females who are pregnant or nursing.
2) Women of childbearing potential not using adequate contraception as per investigator judgment or not willing to comply with contraception for duration of study.
3) Patient had received DM, memantine, other anti-inflammatory medication within 1 week prior to first dose of double-blind medication, such as cyclo-oxygenase 2 (Cox-2) inhibitors.
4) Clinically significant medical condition e.g., cardiac, hepatic and renal disease with current evidence of poor controlled.
5) Patient had received electroconvulsive therapy (ECT) within 4 weeks prior to the first dose of double-blind medication.
6) Increase in total SGOT, SGPT, BUN and creatinine by more than 3× upper limit of normal.

Measures of Symptomatology

Efficacy will be assessed by the YMRS, HDRS and Side-Effects.

Clinical ratings were performed by research psychiatric professionals who were well-trained and experienced in the rating scales. All assessments were blind to treatment assignment and completed at baseline and at the end of week 1, 2, 4, 8 and 12. Routine laboratory tests, including CBC and biochemistry were checked at baseline and the end of week 12.

Diagnostic and Symptom Evaluation Tools (1) Chinese Version of the Modified Schedule of Affective Disorder and Schizophrenia-Lifetime (SADS-L)

The Chinese version of the modified SADS-L was a semi-structured interview aimed at formulating the main diagnosis based upon DSM-IV criteria. We used this modified version of the SADS-L as the gold standard for diagnosis.

(2) Young Mania Rating Scale (YMRS) and 17-item Hamilton Depression Rating Scale (HDRS)

Those clinically suspected of having a mood disorder were invited to be interviewed with the Chinese version SADS-L and diagnosed as having BP-II. The severity of current symptoms was assessed by using the YMRS and HDRS. The diagnosis of a mood disorder was made according to DSM-IV criteria, except for BP-II, for which we used a 2-day instead of a 4-day duration for hypomania.

(3) Side-Effects Checklist

The severity of side effects was evaluated by using the Chinese version of Side-Effects Checklist which derived from Psychiatric Rating and Diagnostic Instruments (TRIMS, 1972) and included 7 categories as follows: 1) Mental Status; 2) Genito-Urinary; 3) Cardiovascular; 4) Head-Neck; 5) Extremities; 6) Skin; 7) Gastrointestinal. The order of severity was 3-point: 0=Not present; 1=Mild or occasional; 2=Moderated or occurs several times a day; 3=Severe or persistent.

Laboratory Assessments

Serum levels of DM, memantine, plasma BDNF, and cytokines were measured. 10 millimeters of whole blood was drawn and collected from the antecubital vein. Plasma were isolated from the whole blood after the 3000 g centrifugation at 4° C. for 15 min and stored at −80° C. immediately. Plasma BDNF, CRP, TNF-α, were measured at baseline, 1, 2, 4, 8 and 12 weeks and quantified using the enzyme-linked immunosorbent assays (ELISAs). Cytokine levels were quantified using an antibody pair assay system (Flexia; BioSource Intl., Camarillo, Calif.). Sample processing and data analysis were done according to the manufacturer's instructions. The low limit sensitivity was 0.126 pg/ml, 0.057 pg/ml, and 20 pg/ml for TNF-α, IL-1β, and BDNF respectively. Finally, HPLC with UV detector and therapeutic drug monitoring (TDM) was used to measure the plasma DM and VPA level respectively.

Symptom severity, immunological parameters (plasma tumor necrosis factor α (TNF-α) and C-reactive protein (CRP)) and plasma brain derived neurotrophic factor (BDNF) were examined regularly. Metabolic profiles (cholesterol, triglyceride, HbA1C, fasting serum glucose, body mass index [BMI]) were measured at baseline and 2, 8, and 12 weeks. Concomitant benzodiazepine medication (lorazepam <8 mg) was used for nighttime sedation, and to treat agitation and insomnia during the study. Up to 20 mg/daily of fluoxetine was permitted for associated depressive symptoms.

Statistical Analysis

The analyses were conducted using SPSS.18.0 windows version.

1. Participants who completed this study for at least 8 weeks of treatment, the data was conducted using Intent to Treatment (ITT) and last observation carried forward (LOCF).

2. Demographic characteristics were analyzed using Chi-Square for the nominal variables.

3. Multi-variate analyses: applying multiple regression and logistic regression to analyze each variable (including demographics, symptom severity, plasma BDNF, cytokines, change of lipid profiles and response to medication treatment) in prediction of prognosis in patients with BP-II.

4. The effect size conventions in power analysis were determined according to Buchner et al. (1996) as follows: small effect size=0.10, medium effect size=0.30, large effect size=0.50 for the test; and small effect size=0.02, medium effect size=0.15, large effect size=0.35 for the multiple regression model (alpha=0.05).

The demographic and clinical characteristics of the patients, their baseline YMRS and HDRS scores, and their baseline cytokine levels were compared between groups using one-way analysis of variance (ANOVA) for continuous variables, and $\chi^2$ tests for categorical variables. Data are means±standard deviation (SD). Both CRP and TNF-α levels were distributed erratically and showed a significant level of positive skew (Table 1). Arithmetic transformations were used to produce approximately normal distributions for further analysis; log (x+1) was used for cytokine levels.

The intent to-treat (ITT) analysis set included all randomized patients who received at least one dose of study drug, and had one baseline assessment and at least one after baseline. All the outcome variables were analyzed in the ITT set, including HDRS, YMRS, cytokine levels, plasma BDNF levels and metabolic parameters; missing data was filled in using the last observation carried forward (LOCF) method.

The overall within-group changes of each outcome over the 12 weeks were analyzed by paired sample t-test. To compare the difference in outcomes of add-on medication (DM30, MM5, and DM30+MM5) versus placebo, generalized estimating equation (GEE) was adopted. A total of 10 models ran with each outcome as a dependent variable. In each model, add-on medication received (DM30, MM5, and DM30+MM5 vs. controls), treatment duration, treatment received X treatment duration, gender, and age were included as independent variables. The covariance structure employed was autoregressive (AR(1)) model. The placebo group was used as reference group. The interaction term of treatment received X treatment duration was regarded as effect of add-on DM30, MM5, and DM30+MM5. To analyze correlations between cytokines, BDNF and metabolic profiles, GEE analysis was used as well. Plasma cytokines and BDNF were set as independent variables while the metabolic profile were set as dependent variables; controlling for time effects (treatment period from baseline to week 12), gender and age, and clinical severity. SPSS 22.0 for Windows was used for statistical computations. Significance was set at p<0.05.

Results

Figure 1:
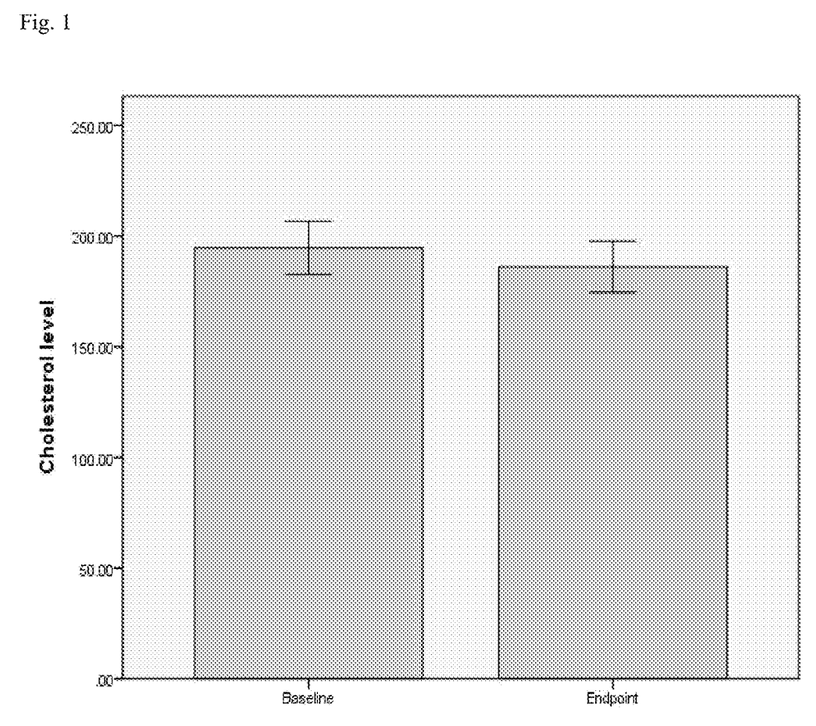
FIG. 1 shows decreasing tendency of total cholesterol over 4-week of treatment (194.70±39.49 vs. 186.16±37.95 mg/dl; P=0.09).

Three hundred and twelve patients were initially screened. Fifty-one patients were excluded due to not meeting inclusion criteria (n=32) and refusal to participate (n=10). Two hundred seventy patients with BP-II were randomly assigned to groups given DM30 (n=69), MM5 (n=66), DM30+MM5 (n=66) and placebo (n=69) for 12 weeks. All patients were first diagnosed. One hundred thirty-six (50.4%) of the 270 patients completed the double blind phase, and 134 (49.6%) dropped out (FIG. 1). Their reasons for discontinuing the study were as follows: One with poor tolerance to a side effect (dizziness) in the MM5 group, and 133 patients loss of follow-up for an unknown reason (DM30, n=30; MM5, n=35; DM30+MM5=26; placebo, n=42). All patients were treated with benzodiazepines (range: 2-6 mg/day).

The demographic and clinical characteristics, baseline HDRS and YMRS scores, cytokine/BDNF levels and metabolic profiles of the patients were similar in the 4 treatment groups at baseline (Table 1). After 12 weeks of treatment, the mean within group changes in every outcome are shown in Table 2. Significant within group changes in clinical severity (HDRS and YMRS) in all treatment groups were found (Table 2). Significant decreased CRP and increased BDNF levels were also found in the DM30+MM5 group. Significant improved BDNF level was also found in the DM30 group. In the placebo group, significant decreases in total cholesterol and LDL-C levels were found after 12-week of treatment.

Figure 2:
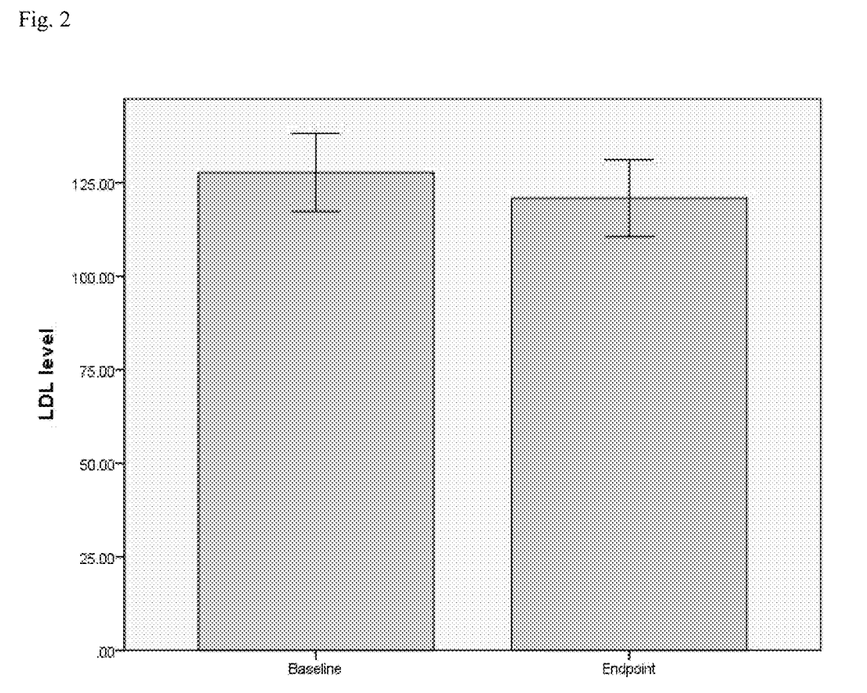
FIG. 2 shows decreasing tendency of low density lipid protein (LDL) over 4-week of treatment (127.70±34.24 vs. 120.84±34.013 mg/dl; P=0.13).
Figure 3:
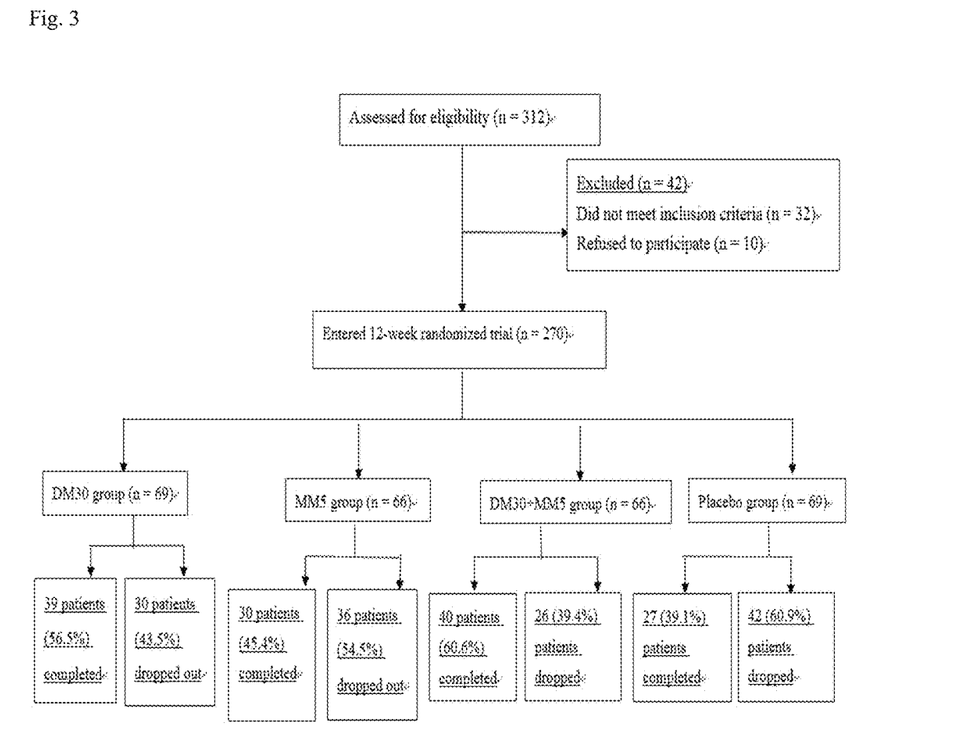
FIG. 3 is a consort diagram to show how patients with bipolar disorder II are recruited for conducting the experiments.
Figure 4:
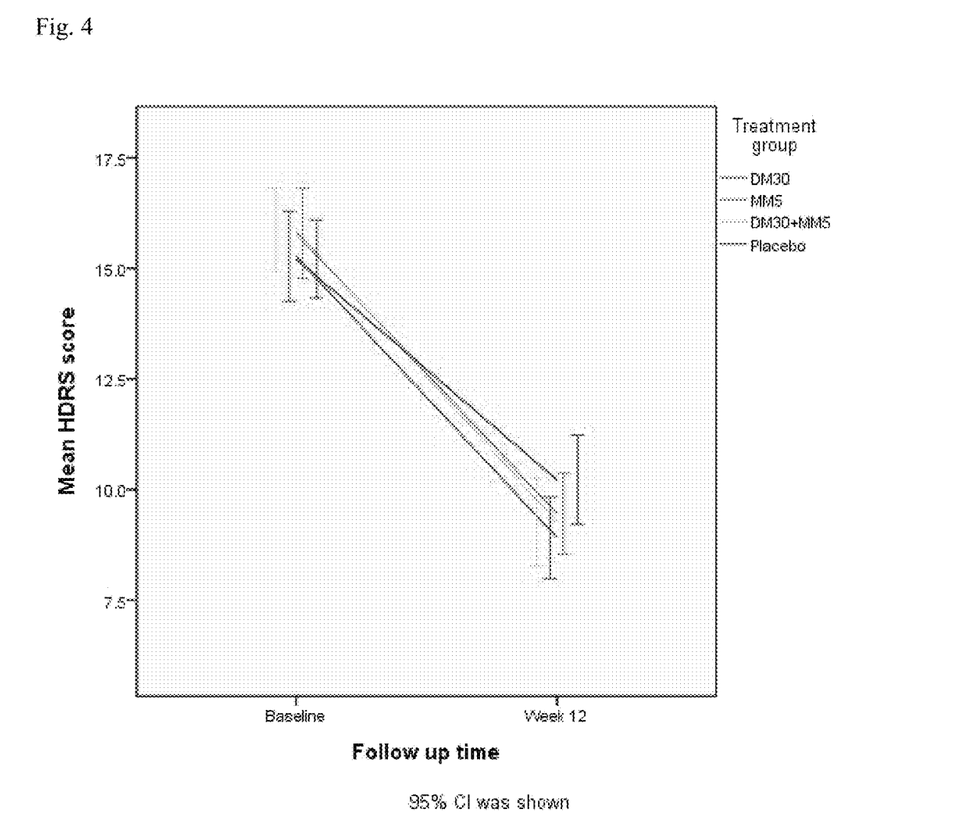
FIG. 4 shows the difference in depressive symptoms of add-on medication (DM30, MM5, and DM30+MM5) versus placebo in BP-II patients.
Figure 5:
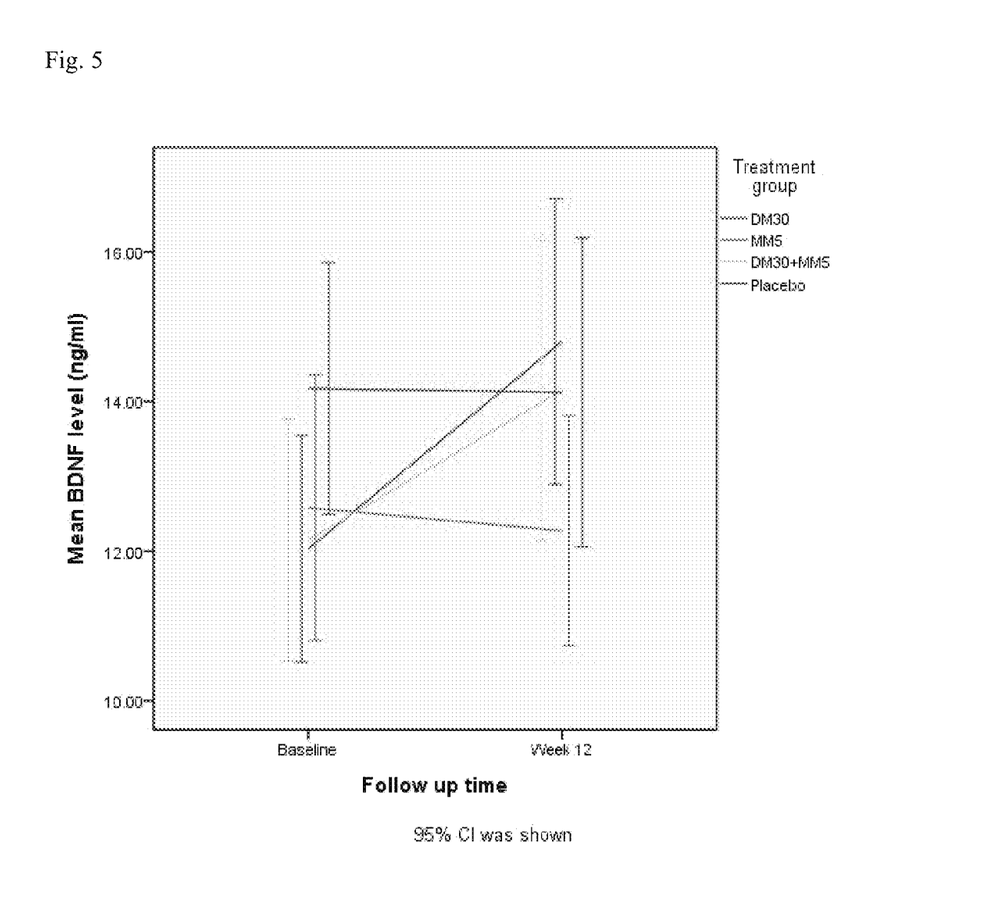
FIG. 5 shows the difference in plasma BDNF level of add-on medication (DM30, MM5, and DM30+MM5) versus placebo in BP-II patients

The treatment effect of DM30, MM5, and DM30+MM5 to the placebo group was compared by using the GEE analysis (Table 3). A significant difference in change of HDRS score was found in the DM30+MM5 group compared with the placebo group after 12 weeks of treatment (P=0.03) (Table 3)(FIG. 2); a trend of difference in change of YMRS score in the DM30+MM5 group was also found, although not significant. A significant difference in increase of BDNF levels was also found in the DM30+MM5 group compared with the placebo group (P=0.04)(FIG. 3).

For the correlation between change of plasma cytokines/BDNF with clinical severity and metabolic parameters, the change in plasma BDNF level was significantly associated with the changes in total cholesterol (P=0.04) levels. The change in CPR level was significantly associated with change in YMRS scores (P=0.03), HDL-C (P=<0.001) and triglyceride levels (P=<0.001). In addition, the change in TNF-α level was also significantly associated with change in HDL-C (P=0.01) and triglyceride levels (P=0.001) (Table 4).

TABLE 1

Characteristics of the BP-II patients in different treatment groups at baseline.

| Treatment groups | DM30 | MM5 | DM30 + MM5 | Placebo | F or $\chi^2$ | P-value |
|---|---|---|---|---|---|---|
| N | 69 | 66 | 66 | 69 | | |
| Age (years) (mean, SD) | 36.3 ± 13.3 | 37.4 ± 14.0 | 35.7 ± 13.2 | 35.2 ± 13.8 | 0.32 | 0.81 |
| Gender (M/F) | 34/35 | 27/39 | 22/44 | 34/35 | 4.83 | 0.19 |
| Onset age (years) (mean, SD) | 15.4 ± 5.0 | 14.8 ± 5.0 | 14.9 ± 4.3 | 13.6 ± 2.8 | 1.79 | 0.15 |
| HDRS (mean, SD) | 15.3 ± 4.2 | 15.8 ± 4.2 | 15.9 ± 3.8 | 15.2 ± 3.7 | 0.51 | 0.68 |
| YMRS (mean, SD) | 13.1 ± 3.2 | 13.5 ± 2.9 | 13.5 ± 3.4 | 13.6 ± 2.8 | 0.34 | 0.80 |
| TNF-α (mean, SD) (pg/mL) | 1.7 ± 1.3 | 2.1 ± 1.8 | 1.8 ± 1.3 | 1.9 ± 1.6 | 0.88 | 0.45 |
| CRP (mean, SD) (ng/ml) | 1658.4 ± 1346.6 | 1635.4 ± 1237.1 | 1814.5 ± 1489.6 | 1878.0.5 ± 1525.0 | 0.47 | 0.70 |
| BDNF (mean, SD) (ng/ml) | 12.6 ± 7.3 | 12.6 ± 6.9 | 12.1 ± 6.3 | 14.0 ± 6.6 | 0.90 | 0.44 |
| Total cholesterol (mean, SD) (mg/dL) | 179.8 ± 44.9 | 172.5 ± 29.9 | 182.0 ± 39.9 | 180.9 ± 39.8 | 0.71 | 0.50 |
| HDL-C (mean, SD) (mg/dL) | 55.9 ± 15.2 | 57.5 ± 16.6 | 59.4 ± 12.7 | 55.0 ± 17.9 | 1.00 | 0.40 |
| LDL-C (mean, SD) (mg/dL) | 117.4 ± 33.4 | 109.0 ± 28.0 | 117.5 ± 36.5 | 114.2 ± 31.4 | 0.97 | 0.41 |
| Triglyceride (mean, SD) (mg/dL) | 106.0 ± 68.5 | 94.6 ± 51.2 | 91.8 ± 44.1 | 119.6 ± 86.4 | 1.84 | 0.14 |
| Glucose (mean, SD) (mg/dL) | 96.1 ± 37.7 | 88.8 ± 9.6 | 88.2 ± 13.7 | 92.7 ± 22.5 | 1.60 | 0.19 |

SD: standard deviation;
HDRS: 17-item Hamilton Depression Rating Scale;
YMRS: Young Mania Rating Scale;
TNF-α: tumor necrosis factor α;
CRP: C-reactive protein;
BDNF: brain derived neurotrophic factor;
HDL-C: high-density lipoprotein cholesterol;
LDL-C: low-density lipoprotein cholesterol;
DM30: dextromethorphan (30 mg/day);
MM5: memantine (5 mg/day);
DM30 + MM5: dextromethorphan (30 mg/day) combined with memantine (5 mg/day)

TABLE 2

Within group changes (baseline minus endpoint) in clinical characteristics of the BP-II patients in different treatment groups after 12-week of follow-up.

| Treatment groups Change | DM30 Mean ± SD | P-value | MM5 Mean ± SD | P-value | DM30 + MM5 Mean ± SD | P-value | Placebo Mean ± SD | P-value |
|---|---|---|---|---|---|---|---|---|
| Primary outcomes | | | | | | | | |
| HDRS | 6.4 ± 4.7 | <0.001** | 6.3 ± 4.9 | <0.001** | 6.6 ± 4.6 | <0.001** | 5.0 ± 4.1 | <0.001** |
| YMRS | 4.7 ± 3.4 | <0.001** | 4.6 ± 3.9 | <0.001** | 4.9 ± 4.0 | <0.001** | 3.6 ± 4.1 | <0.001** |
| Cytokines and BDNF | | | | | | | | |
| TNF-α (pg/mL) | 0.1 ± 2.5 | 0.76 | 0.3 ± 1.8 | 0.09 | 0.3 ± 1.4 | 0.16 | −0.2 ± 1.6 | 0.87 |
| CRP (ng/ml) | 10.9 ± 1290.3 | 0.20 | −12.6 ± 1269.4 | 0.98 | 371.3 ± 1157.9 | 0.005** | 20.9 ± 978.8 | 0.17 |
| BDNF (ng/ml) | −2.3 ± 8.3 | 0.035* | 0.3 ± 7.6 | 0.75 | −2.2 ± 8.2 | 0.044* | 0.09 ± 8.9 | 0.94 |
| Metabolic parameters | | | | | | | | |
| Total cholesterol (mg/dL) | −0.1 ± 28.7 | 0.98 | 0.5 ± 24.5 | 0.90 | 0.6 ± 28.6 | 0.89 | 8.3 ± 24.6 | 0.034* |
| HDL-C (mg/dL) | 1.6 ± 10.2 | 0.28 | 2.4 ± 8.7 | 0.10 | −10.7 ± 82.4 | 0.41 | 1.3 ± 7.2 | 0.26 |
| LDL-C (mg/dL) | −0.9 ± 23.1 | 0.79 | 2.6 ± 22.0 | 0.48 | 4.6 ± 24.4 | 0.23 | 7.7 ± 21.9 | 0.034* |
| Triglyceride (mg/dL) | −11.6 ± 168.4 | 0.68 | −10.7 ± 38.7 | 0.17 | −2.5 ± 44.3 | 0.73 | −14.0 ± 57.0 | 0.20 |
| Glucose (mg/dL) | 9.0 ± 38.1 | 0.10 | −3.3 ± 22.6 | 0.33 | 2.8 ± 9.9 | 0.06 | 2.0 ± 14.2 | 0.34 |

SD: standard deviation;
HDRS: 17-item Hamilton Depression Rating Scale;
YMRS: Young Mania Rating Scale;
TNF-α: tumor necrosis factor a;
CRP: C-reactive protein;
BDNF: brain derived neurotrophic factor;
HDL-C: high-density lipoprotein cholesterol;
LDL-C: low-density lipoprotein cholesterol;
DM30: dextromethorphan (30 mg/day);
MM5: memantine (5 mg/day);
DM30 + MM5: dextromethorphan (30 mg/day) combined with memantine (5 mg/day).
*P < 0.05;
**P < 0.01.
The difference between baseline and endpoint after 12 week of follow-up analyzed by paired sample t-test.

TABLE 3

Difference in outcomes of add-on medication (DM30, MM5, and DM30 + MM5) versus placebo in BP-II patients

| | B | Wald $\chi^2$ | P-value |
|---|---|---|---|
| HDRS[×] | | | |
| DM30 | −1.38 | 3.36 | 0.07 |
| MM5 | −1.33 | 2.96 | 0.09 |
| DM30 + MM5 | −1.60 | 4.61 | 0.03* |
| YMRS[×] | | | |
| DM30 | −1.00 | 2.44 | 0.12 |
| MM5 | −0.98 | 2.07 | 0.15 |
| DM30 + MM5 | −1.32 | 3.68 | 0.06 |
| TNF-α[§] | | | |
| DM30 | −0.04 | 0.14 | 0.71 |
| MM5 | −0.15 | 2.00 | 0.16 |
| DM30 + MM5 | −0.07 | 0.68 | 0.41 |
| CRP[§] | | | |
| DM30 | 0.05 | 0.40 | 0.53 |
| MM5 | 0.09 | 1.18 | 0.28 |
| DM30 + MM5 | −0.05 | 0.41 | 0.52 |
| BDNF[§] | | | |
| DM30 | 2.94 | 2.97 | 0.09 |
| MM5 | 0.02 | <0.001 | 0.99 |
| DM30 + MM5 | 3.44 | 4.23 | 0.04* |
| Total Cholesterol[§] | | | |
| DM30 | 6.95 | 1.60 | 0.21 |
| MM5 | 3.14 | 0.38 | 0.54 |
| DM30 + MM5 | 4.37 | 0.60 | 0.44 |

TABLE 3-continued

Difference in outcomes of add-on medication
(DM30, MM5, and DM30 + MM5)
versus placebo in BP-II patients

|  | B | Wald $\chi^2$ | P-value |
|---|---|---|---|
| HDL-C[§] | | | |
| DM30 | 0.79 | 0.11 | 0.74 |
| MM5 | −0.07 | 0.001 | 0.98 |
| DM30 + MM5 | 14.45 | 1.04 | 0.31 |
| LDL-C[§] | | | |
| DM30 | 8.80 | 3.35 | 0.07 |
| MM5 | 4.45 | 0.80 | 0.37 |
| DM30 + MM5 | 3.21 | 0.38 | 0.54 |
| Triglyceride[§] | | | |
| DM30 | 28.08 | 0.94 | 0.33 |
| MM5 | 8.81 | 0.29 | 0.59 |
| DM30 + MM5 | 11.69 | 0.52 | 0.47 |
| Glucose[§] | | | |
| DM30 | −5.33 | 0.90 | 0.34 |
| MM5 | 7.63 | 2.82 | 0.09 |
| DM30 + MM5 | −0.31 | 0.02 | 0.90 |

B: standardized coefficient;
HDRS: 17-item Hamilton Depression Rating Scale;
YMRS: Young Mania Rating Scale;
TNF-α: tumor necrosis factor α;
CRP: C-reactive protein;
BDNF: brain derived neurotrophic factor;
HDL-C: high-density lipoprotein cholesterol;
LDL-C: low-density lipoprotein cholesterol;
DM30: dextromethorphan (30 mg/day);
MM5: memantine (5 mg/day);
DM30 + MM5: dextromethorphan (30 mg/day) combined with memantine (5 mg/day).
[X]Using the placebo group as reference group, controlling for age, gender, treatment duration. The data shown is the interaction term and treatment group and treatment duration.
[§]Using the placebo group as reference group, controlling for age, gender, treatment duration, HDRS and YMRS. The data shown is the interaction term and treatment group and treatment duration.
*P < 0.05.

TABLE 4

Correlation between TNF-α, CRP and BDNF with clinical symptoms and metabolic parameters

| | TNF-α | | | CRP | | | BDNF | | |
|---|---|---|---|---|---|---|---|---|---|
| | B | Wald $\chi^2$ | P-value | B | Wald $\chi^2$ | P-value | B | Wald $\chi^2$ | P-value |
| HDRS | 0.45 | 1.07 | 0.30 | 0.22 | 0.62 | 0.43 | 0.11 | 1.94 | 0.16 |
| YMRS | 0.20 | 0.32 | 0.57 | 0.72 | 4.82 | 0.03* | −0.01 | 0.30 | 0.58 |
| Cholesterol | −1.83 | 0.28 | 0.60 | 1.98 | 0.32 | 0.58 | 0.52 | 4.20 | 0.04* |
| HDL-C | −5.34 | 6.24 | 0.01* | −11.61 | 24.82 | <0.001** | 0.02 | 0.02 | 0.89 |
| LDL-C | −1.91 | 0.41 | 0.53 | 5.51 | 3.19 | 0.07 | 0.38 | 2.69 | 0.10 |
| Triglyceride | 22.78 | 10.67 | 0.001** | 34.58 | 22.38 | <0.001** | 0.97 | 3.46 | 0.06 |
| Fasting Sugar | −6.37 | 1.30 | 0.26 | 0.73 | 0.13 | 0.72 | 0.27 | 3.41 | 0.07 |

B: standardized coefficient;
HDRS: 17-item Hamilton Depression Rating Scale;
YMRS: Young Mania Rating Scale;
HDL-C: high-density lipoprotein cholesterol;
LDL-C: low-density lipoprotein cholesterol.
*P < 0.05;
**P < 0.01 and change of cholesterol was monitored only over 4 weeks. The decreasing tendency of total cholesterol over 4-week of treatment (194.70±39.49 vs. 186.16±37.95 mg/dl; P=0.09) (FIG. 1), as well as the low density lipid protein (LDL) (127.70±34.24 vs. 120.84±34.013 mg/dl; P=0.13) (FIG. 2) was found. It showed that dextromethorphan decreased cholesterol and LDL in human, thus had great potential in treating coronary heart disease, stroke, peripheral vascular disease, type 2 diabetes, high blood pressure, or hypercholesterelmia.

One skilled in the art readily appreciates that the present invention is well adapted to carry out the objects and obtain the ends and advantages mentioned, as well as those inherent therein. The compositions, processes and methods for producing them, and uses thereof are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional Example 2

This example was a clinical trial for the treatment of bipolar II disorder using 30 mg/day of dextromethorphan (off label use) adding on to depakine (plasma level 50-100 ug/dl). 44 patients with bipolar II disorder were recruited, features, modification and variation of the concepts herein disclosed may be resorted to by those skilled in the art, and that such modifications and variations are considered to be within the scope of this invention as defined by the appended claims.

What is claimed is:

1. A method of treating a subject suffering from bipolar II disorder, comprising administering to said subject a therapeutically effective amount of valproic acid and a combination of dextromethorphan and memantine, wherein the dose of dextromethorphan is 30 mg/day or less and the dose of memantine is 5 mg/day or less, which is a low dose not sufficient to work as a N-methyl-D-aspartate (NMDA) receptor antagonist.

2. The method of claim 1, wherein the combination of dextromethorphan and memantine produces a synergistic effect in treating bipolar II disorder.

3. A composition for treating bipolar II disorder, which comprises valproic acid and a combination of dextromethorphan and memantine, wherein the dose of dextromethorphan is 30 mg/day or less and the dose of memantine is 5 mg/day or less, which is a low dose not sufficient to work as a N-methyl-D-aspartate (NMDA) receptor antagonist.

* * * * *